(12) United States Patent
Bornzin

(10) Patent No.: US 7,925,347 B1
(45) Date of Patent: Apr. 12, 2011

(54) ASSESSMENT OF CARDIAC OUTPUT BY IMPLANTABLE MEDICAL DEVICE

(75) Inventor: Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 400 days.

(21) Appl. No.: 11/945,025

(22) Filed: Nov. 26, 2007

(51) Int. Cl.
A61N 1/362 (2006.01)

(52) U.S. Cl. .......................... 607/22; 607/18

(58) Field of Classification Search .............. 607/18–25; 600/303–336
See application file for complete search history.

(56) References Cited

U.S. PATENT DOCUMENTS

| | | | |
|---|---|---|---|
| 4,949,724 A | 8/1990 | Manhutte et al. | |
| 5,119,813 A | 6/1992 | Cohen | |
| 5,139,020 A * | 8/1992 | Koestner et al. | 607/24 |
| 5,156,148 A | 10/1992 | Cohen | |
| 5,188,106 A | 2/1993 | Nappholz et al. | |
| 5,241,966 A | 9/1993 | Finkelstein et al. | |
| 5,891,176 A | 4/1999 | Bornzin | |
| 6,162,180 A | 12/2000 | Miesel et al. | |
| 6,409,675 B1 | 6/2002 | Turcott | |
| 6,463,324 B1 | 10/2002 | Ben-Haim et al. | |
| 6,928,324 B2 * | 8/2005 | Park et al. | 607/20 |
| 7,164,948 B2 * | 1/2007 | Struble et al. | 607/22 |
| 2002/0077536 A1 * | 6/2002 | Diab et al. | 600/323 |
| 2003/0199956 A1 | 10/2003 | Struble et al. | |
| 2004/0220455 A1 | 11/2004 | Lowe et al. | |
| 2004/0220637 A1 * | 11/2004 | Zdeblick et al. | 607/17 |
| 2005/0054905 A1 | 3/2005 | Corl et al. | |
| 2006/0178912 A1 * | 8/2006 | Ferraro et al. | 705/3 |
| 2006/0240150 A1 * | 10/2006 | Delaney et al. | 426/74 |

FOREIGN PATENT DOCUMENTS

WO 0130234 A2 5/2001

OTHER PUBLICATIONS

Ohlsson, A. et al., "Long-term recording of cardiac output via an implantable haemodynamic monitoring device," Eur Heart J 1996;17:1902-1910.

NonFinal Office Action, mailed Aug. 22, 2007: Related U.S. Appl. No. 10/938,173.

NonFinal Office Action, mailed Feb. 7, 2007: Related U.S. Appl. No. 10/938,173.

* cited by examiner

Primary Examiner — Carl H Layno
Assistant Examiner — Paula J Stice

(57) ABSTRACT

An implantable medical device calculates cardiac output on a repeated basis based on acquired cardiac information that relates to one or more parameters of the Fick equation, including venous oxygen saturation, arterial oxygen saturation, estimated oxygen consumption and hemoglobin information. In some aspects, the estimated oxygen consumption may be based on the activity of a patient. For example, respiratory-related information and/or temperature related information may be used to determine the activity level of the patient. In addition, trends relating to heart function may be identified based on cardiac output calculations that are generated over time.

14 Claims, 8 Drawing Sheets

ASSESSMENT OF CARDIAC OUTPUT BY IMPLANTABLE MEDICAL DEVICE

CROSS REFERENCE TO RELATED APPLICATIONS

This application is related to copending U.S. patent application Ser. No. 10/938,173, filed Sep. 10, 2004, titled "Analysis of Metabolic Gases by an Implantable Cardiac Device for the Assessment of Cardiac Output."

TECHNICAL FIELD

This application relates generally to implantable medical devices and more specifically, but not exclusively, to implantable medical devices that determine cardiac output.

BACKGROUND

In conjunction with the diagnosis and treatment of certain cardiac conditions, various types of hemodynamic information may be acquired to determine how effectively the patient's heart is functioning. For example, a cardiac monitoring system may acquire information relating to oxygen saturation, blood pressure, cardiac output, and other parameters. Under some circumstances, a determination of cardiac output (e.g., the amount of blood pumped by the heart per minute) may be a particularly useful measure of how effectively the heart is working.

Cardiac output ("CO") for a patient may be estimated through the use of the Fick equation:

$$CO = \frac{VO_2}{(SaO_2 - SvO_2) \cdot 1.34 \cdot Hb \cdot 1000} \text{(liters/minute)} \quad \text{EQUATION 1}$$

Here, $\dot{V}O_2$ relates to the patient's oxygen consumption, $SaO_2$ relates to the patient's arterial oxygen saturation, $SvO_2$ relates to the patient's venous oxygen saturation, and $Hb$ relates to the total hemoglobin in the patient's blood.

SUMMARY

A summary of sample aspects of the disclosure follows. It should be understood that any reference to the term aspects herein may refer to one or more aspects of the disclosure.

The disclosure relates in some aspect to determining cardiac output. For example, an implantable medical device may estimate cardiac output on a repeated basis based on physiological information that is acquired by the implantable medical device. In some aspects, the acquired information relates to one or more parameters of the Fick equation.

The disclosure relates in some aspects to generating estimates of cardiac output based on patient activity. For example, estimates of cardiac output may be generated over a period of time whereby each estimate may be based on the activity level of the patient at the time of the estimate. In some embodiments the implantable medical device may determine the activity level of the patient by acquiring acceleration-related information, respiratory-related information, temperature-related information, or heart-rate-related information.

The disclosure relates in some aspects to monitoring trends relating to heart function (e.g., heart failure) based on estimates of cardiac output that are generated over time. For example, an implantable medical device may generate a histogram based on a series of estimates of cardiac output. Trends relating to progression or aggression of heart failure may then be identified based on the histogram information.

The disclosure relates in some aspects to an implantable medical device that acquires hemoglobin-related information. For example, the device may acquire hemoglobin-related information through the use of optic-based blood analysis or blood impedance measurements. The implantable medical device may then use the hemoglobin-related information to generate an estimate of cardiac output.

BRIEF DESCRIPTION OF THE DRAWINGS

These and other features, aspects, and advantages will be more fully understood when considered with respect to the following detailed description, the appended claims, and the accompanying drawings, wherein:

Figure 1:
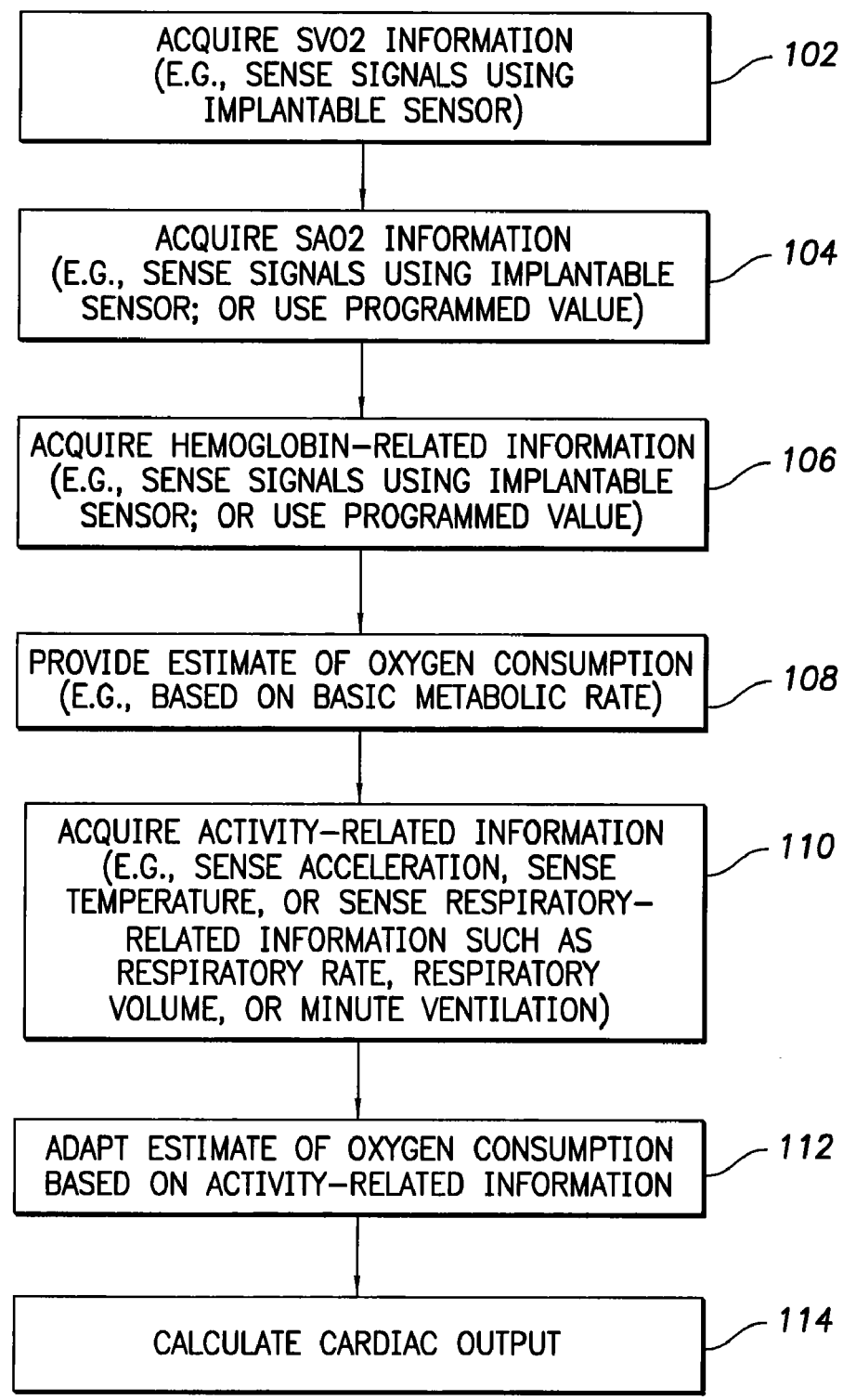
FIG. 1 is a simplified flowchart of an embodiment of operations that may be performed to derive an indication of cardiac output.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The description that follows sets forth one or more illustrative embodiments. It will be apparent that the teachings herein may be embodied in a wide variety of forms, some of which may appear to be quite different from those of any disclosed embodiment. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

The disclosure relates in some aspects to providing an indication (e.g., an estimate) of cardiac output based on one or more parameters that are acquired by an implantable medical device. Here, the indication of cardiac output may be correlated with various levels of activity of a patient. For example, the implantable medical device may determine cardiac output levels when the patient is resting, when the patient is engaged in normal activity, when the patient is engaged in various levels of exercise, or when the activity level the patient is engaged in is at some other level. In some aspects, this cardiac output information may be tracked over time so that the patient's therapy may be adapted based on any trends that are indicated by the cardiac output information.

Figure 2:
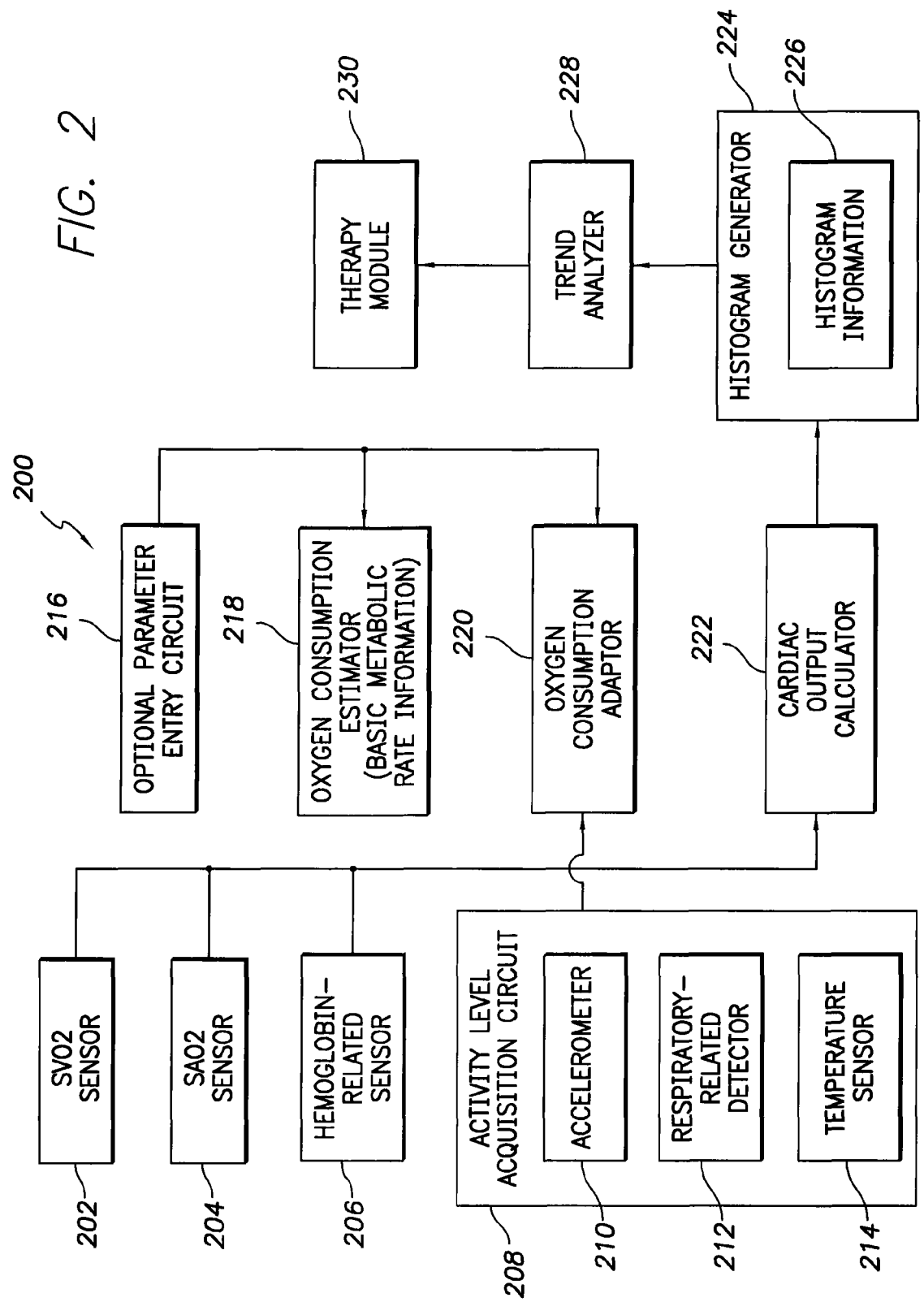
FIG. 2 is a simplified block diagram of an embodiment of a system that may perform cardiac output-related operations.

Referring initially to FIGS. 1 and 2, several sample aspects of a method of providing an indication of cardiac output (corresponding to metabolic demand) and functional components that may be employed to provide such an indication will be described. Briefly, FIG. 2 depicts a system 200 including components 202-216 for acquiring or otherwise providing information that may be used to determine cardiac output, components 218-222 that may be employed to generate an indication of cardiac output, and components 224-230 that may process or otherwise utilize cardiac output information.

The system 200 may generate the indication of cardiac output based on the Fick equation. Accordingly, the system 200 may provide an estimate of cardiac output based on mixed venous oxygen saturation ($SvO_2$), an estimate of oxygen consumption ($VO_2$), arterial oxygen saturation ($SaO_2$), and total hemoglobin in the blood (Hb). Accordingly, as will be discussed in more detail below, the apparatus 200 may include various components for acquiring or otherwise providing one or more of these parameters and for deriving cardiac output based on the Fick equation.

In some implementations one or more of the components of the system 200 may be implantable. For example, an implantable medical device (e.g., an implantable cardiac stimulation device) may include various components for determining cardiac output based on information provided by one or more components of the implantable medical device, one or more other implantable devices (e.g., implantable sensors), or some other device.

For convenience, the operations of FIG. 1 (or any other operations discussed or taught herein) may be described as being performed by specific components (e.g., the components of FIG. 2). It should be appreciated, however, that these operations may be performed by other types of components and may be performed using a different number of components. It also should be appreciated that one or more of the operations described herein may not be employed in a given implementation.

As represented by block 102 of FIG. 1, an $SvO_2$ sensor 202 acquires mixed venous oxygen saturation information for the cardiac output estimation process. In some implementations the sensor 202 may comprise an implantable sensor. For example, the sensor 202 may be implanted in a chamber of the heart or other vasculature of the cardiovascular system (e.g., in the right ventricle, pulmonary artery, or right atrium). In such a case, the sensor 202 may be coupled to an implantable medical device via an implantable lead or some other suitable mechanism to provide the $SvO_2$ information to the medical device. The sensor 202 may comprise an implantable oximeter (e.g., utilizing reflectance oximetry), or some other suitable signal acquisition device, such as an implantable electromechanical Clark Oxygen Sensor. An example of an $SvO_2$ sensor is described in U.S. Pat. No. 5,676,141, the disclosure of which is hereby incorporated by reference herein.

As represented by block 104 of FIG. 1, in some embodiments the system 200 may include an $SaO_2$ sensor 204 that acquires atrial oxygen saturation information for the cardiac output estimation process. The sensor 204 also may comprise an implantable sensor that is implanted in a chamber of the heart or other vasculature of the cardiovascular system. Again, the sensor 204 may be coupled to an implantable medical device via an implantable lead or some other suitable mechanism to provide the $SaO_2$ information to that device. The sensor 204 may comprise a PPG sensor or some other suitable acquisition device. Examples of PPG sensors are described in U.S. Pat. Nos. 6,491,639 and 6,731,967, the disclosure of each of which is hereby incorporated by reference herein.

In some embodiments a sensor may not be used to acquire atrial oxygen saturation information. For example, in some implementations atrial oxygen saturation may be assumed to be constant. Here, $SaO_2$ may be specified as a value within a range of 98% to 99% or some other suitable range (e.g., 93% to 100%). In such a case, the $SaO_2$ value may be programmed into the system 200 through the use of an optional parameter entry circuit 216 or some other suitable component. As an example, the parameter entry circuit 216 may comprise a data memory for storing an $SaO_2$ parameter. In addition, the parameter entry circuit 216 may include appropriate functionality that enables a person or another device to enter parameter information into the data memory. For example, as discussed below in conjunction with FIG. 8 the system 200 may include a receiver that is configured to receive information from another device (e.g., a programmer device) either before or after the system 200 is implanted in a patient.

In some implementations the selected value for $SaO_2$ may be based on an $SaO_2$ measurement. For example, medical personnel may use a pulse oximeter or some other suitable device to measure the $SaO_2$ of a patient and then enter the measured value into the implantable device.

In some implementations an $SaO_2$ value may be automatically provided to an implantable device. For example, an external $SaO_2$ measurement system may acquire the $SaO_2$ information and then automatically transfer this information to an implantable device. Here, the external measurement system may be temporary placed against the skin of the patient (e.g., on a finger) during $SaO_2$ parameter acquisition process. In addition, the external measurement system and the implantable device may include appropriate components to transfer information from one device to the other. For example, the devices may communicate via one or more electrical signal-based channels, radio frequency channels, or optical communication channels.

As represented by block 106 of FIG. 1, in some embodiments the system 200 may include a hemoglobin-related sensor 206 that acquires hemoglobin-related information for the cardiac output estimation process. In some implementations the hemoglobin related information may comprise hematocrit ("HCT") information. In such cases, a measured hematocrit value may be converted to hemoglobin value for use in the Fick equation (e.g., 3Hb=HCT).

In some implementations the sensor 206 may comprise an implantable sensor that is implanted in a chamber of the heart or other vasculature of the cardiovascular system. In such a case, the sensor 206 may be coupled to an implantable medical device via an implantable lead or some other suitable mechanism to provide the hemoglobin-related information to that device.

The sensor 206 may be implemented in various ways. In some embodiments the sensor 206 may comprise an optical sensor that generates hemoglobin-related information (e.g., hematocrit information) using optical-based (e.g., reflectance) techniques. For example, the sensor 206 may include two or more light sources that direct light at blood in a given vessel and a light detector that detects the light that is reflected from that blood. Based on the characteristics of the reflected light, an estimate may be made of a corresponding hemoglobin saturation percentage. In some embodiments the sensor 206 measures or estimates hemoglobin-related information by measuring blood impedance. It should be appreciated that the above examples are provided for illustration purposes, and that other techniques may be employed to obtain hemoglobin-related information. An example of a sensor for obtaining hemoglobin-related information is described in U.S. Pat. No. 4,776,340, the disclosure of which is hereby incorporated by reference.

In some implementations the hemoglobin parameter may be assumed to be constant. In such a case, a hemoglobin value may be programmed into the system 200 using the parameter entry circuit 216 (e.g., in a similar manner as discussed above for $SaO_2$) or using some other suitable component.

As represented by block 108 of FIG. 1, an oxygen consumption estimator 218 provides an estimate of oxygen consumption ($\dot{V}O_2$) for the cardiac output estimation process. In some implementations, oxygen consumption of a patient may be estimated from the metabolic requirements (e.g., metabolic rate) of the patient. Metabolic rate may be estimated from the patient's height, weight, sex, percent body weight, waste dimensions, and body type information (e.g., somatotypes: endomorphic, mesomorphic, and ectomorphic). Here, a conversion factor is used to convert metabolic rate to metabolic equivalents ("METs"). Specifically, 1 kilocalorie/kilogram/hour=1 MET=3.5 milliliters of $O_2$/kilogram/minute.

A basic metabolic rate ("BMR") may be estimated using the Harris-Benedict formula. According to this formula, for men BMR=66÷(13.7×weight in kilograms)+(5×height in centimeters)−(6.8×age in years) kilocalories/day. Similarly, for women BMR=655÷(9.6×weight in kilograms)+(1.8×height in centimeters)−(4.7×age in years) kilocalories/day.

A refinement of the Harris-Benedict formula takes the patient's body type into account when estimating BMR. For example, the Katch-McArdle formula provides an estimate of BMR based on a patient's lean body mass. Here, the body composition of the patient may be tested to determine the lean body mass. As this formula accounts for lean body mass, this formula applies to both men and women. According to the Katch-McArdle formula, BMR=370+(21.6×lean mass in kilograms)kilocalories/day.

It should be appreciated that oxygen consumption may be determined (e.g., calculated or estimated) in various ways. For example, in some implementations the oxygen consumption estimator 218 may employ indirect calorimetry to provide BMR information. Here, oxygen consumption may be measured when the patient is at rest. The resulting measured value may then be programmed into the system 200. Alternatively, in some implementations indirect calorimetry may be used to calibrate an estimated BMR used by the system 200.

In some implementations a profile (e.g. a circadian profile) of metabolic rate may be defined based on typical values of metabolic rate for a patient over a period of time (e.g., one day). For example, a patient may typically have a relatively low metabolic rate during normal sleeping hours, a higher metabolic rate during the day, and a somewhat lower metabolic rate during the evening. Thus, in these implementations, a different BMR may be defined for different times of day.

Referring again to FIG. 2, in implementations where BMR is estimated using the above or similar techniques, the oxygen consumption estimator 218 may comprise a data memory for storing the BMR information (e.g., the BMR profile). Here, the BMR information may be programmed into the system 200 using the parameter entry circuit 216 or some other suitable component in a similar manner as discussed above for the other parameters.

Referring now to block 110 of FIG. 1, an estimate of metabolic rate also may be based on patient activity. For example, the system 200 may incrementally adjust BMR (e.g., the value from the BMR profile) based on the current activity level of the patient. In this way, the device may provide an instantaneous BMR that more accurately reflects the patient's oxygen consumption at a given time (e.g., during a given time period).

The system 200 may include one or more implantable components to acquire information relating to patient activity. For example, as represented by the activity level acquisition circuit 208, the system 200 may include an accelerometer 210, a respiratory-related detector 212, a temperature sensor 214, a heart rate sensor (not shown), or some other suitable parameter acquisition component. In some aspects, the activity information obtained using these components at a given point in time may be correlated with a particular activity level (e.g., a level associated with rest, a normal activity level, or one of various levels associated with exercise).

The accelerometer 210 may be implanted within a patient or carried by the patient in some manner to measure acceleration of the patient's body. As an example of the former scenario, the accelerometer 210 may be mounted within an implantable medical device (e.g., an implantable cardiac stimulation device) or positioned elsewhere within the patient.

The acceleration information acquired by the accelerometer 210 at a given point in time may be correlated with a given level or type of activity. For example, an increase in acceleration may correlate to an increase in activity while a decrease in acceleration may correlate to a decrease in activity. In addition, certain acceleration profiles may be associated with certain types of activities such as walking, running, swimming, and so on.

In some embodiments a physical activity sensor may be employed in conjunction with an "activity variance" sensor, which monitors the activity sensor diurnally to detect the low variance in the measurement corresponding to a rest state. For a description of an example of such an activity variance sensor, see U.S. Pat. No. 5,476,483, the disclosure of which is hereby incorporated by reference herein. In addition, in some embodiments activity-related information may relate to the current position of a patient. For example, it may be advantageous to determine certain conditions (e.g. cardiac output) when the patient is known to be lying down.

Referring again to FIG. 2, the respiratory-related detector 212 may be configured to sense various types of signals relating to respiration. For example, in some embodiment the detector 212 may provide a respiration signal by detecting respiration modulation that is present in an intracardiac electrogram ("IEGM") signal. In the some embodiments the detector 212 may measure impedance and extract respiratory information from a resulting impedance signal. For example, respiratory rate or volume may be detected based on an analysis of trans-thoracic impedance sensed between an electrode implanted within the heart and an electrode connected to the housing of an implantable medical device. See, for example, U.S. Pat. No. 6,449,509, the disclosure of which is hereby incorporated by reference herein.

In some embodiments the sensor 212 measures respiratory rate. Here, an increase in respiratory rate may be associated with an increased level of activity, and vice versa. Thus, the respiratory rate at a given point in time may be correlated to a given activity level.

In some embodiments the sensor 212 measures respiratory volume. In these cases, an increase in respiratory volume may be associated with an increased level of activity, and vice versa. The respiratory volume at a given point in time may thus be correlated to a given activity level.

In some embodiments the sensor 212 measures minute ventilation. An increase in minute ventilation also may be associated with an increased level of activity, and vice versa. Thus, the minute ventilation at a given point in time may be correlated to a given activity level.

The temperature sensor 214 may be implanted within a patient or carried by the patient in some manner to measure body temperature. The measured temperature information obtained at a given point in time may then be correlated with a given level of activity. For example, an increase in temperature may correlate to an increase in activity while a decrease in temperature may correlate to a decrease in activity.

The information provided by one or more of the activity acquisition components may be appropriately calibrated to provide a "fine tuned" estimate of any increase or decrease in metabolic requirements associated with changes in the activity level of the patient. In some cases, this calibration may involve associating typical metabolic rates with certain activities. For example, it may be known or determined that a certain activity such as walking, running, swimming, and so on, may correspond to a given metabolic rate. In addition, it may be determined that these activities are associated with unique activity profiles (e.g., acceleration profiles). Thus, upon detection of a given activity profile, an appropriate adjustment may be made to the current estimate of oxygen consumption. Here, this adjustment may be made based on the metabolic rate that is associated with detected activity profile (i.e., associated with a particular activity).

As represented by block 112 of FIG. 1, an acquisition component of the circuit 208 may thus provide an indication of the current level of activity to an oxygen consumption adaptor 220. The oxygen consumption adaptor 220 may thereby determine whether there has been an increase or decrease in activity (e.g., as compared to a prior activity level or a baseline activity level). In the event an increase in activity has been detected, the oxygen consumption adaptor 220 may increase the estimate of oxygen consumption (metabolic requirements) by corresponding amount (e.g., an incremental amount). Conversely, if a decrease in activity has been detected, the oxygen consumption adaptor 220 may decrease the estimate of oxygen consumption by a corresponding amount.

In some embodiments the oxygen consumption adaptor 220 provides the adapted estimate of $\dot{V}O_2$ by multiplying BMR by an activity-based factor K(a). Here, the dimensionless factor K(a) represents a function that is dependent upon an activity-related parameter a. In these cases, the adaptor 220 provides an instantaneous oxygen consumption indication (e.g., an instantaneous metabolic rate) based on the BMR and the associated activity as indicated by the activity parameter a.

In some embodiments the factor K(a) comprises an acceleration-based factor. Here, the parameter a may represent the root mean square acceleration in g units. In some implementations the acceleration-based function K(a) may vary from approximately 0.9 during sleep to approximately 20 during maximal exercise. An example of the use of such a function K(a) is set forth in Equation 2.

$$\dot{V}O_2 = BMR \times K(a) \times (3.5/24) \text{ milliliters } O_2/\text{minute} \quad \text{EQUATION 2}$$

In Equation 2, a may vary from 0 (e.g., at rest) to 1 (e.g., at maximal activity). Here, the lowest accelerometer reading may be correlated to a value of 0 for a, while the highest accelerometer reading may be correlated to a value of 1 for a. For example, a value of 1 for a may correspond to an acceleration reading of 700 milli-g's. In Equation 2, BMR is in units of kilocalories/day. Hence, by dividing BMR by 24 the units are converted to kilocalories per hour.

In some embodiments the factor K(a) comprises a respiratory-based factor. In these cases, the adaptor 220 may provide an instantaneous oxygen consumption indication (e.g., an instantaneous metabolic rate) based on the BMR and respiratory-related factors such as respiratory rate, respiratory volume, or minute ventilation. Equation 3 sets forth an example of a generalized function K(a) that may based on respiration or some other suitable parameter (e.g., temperature, heart rate, etc.).

$$\dot{V}O_2 = BMR \times K(a) = 28 \times a + 0.9 \quad \text{EQUATION 3}$$

Again, a may vary from 0 (e.g., at rest) to 1 (e.g., at maximal activity). Consequently, in this example $\dot{V}O_2$ may vary from a value that is slightly below BMR to a value that is 28 times BMR. Here, the lowest possible respiratory rate (or respiratory volume, temperature, etc.) may be correlated to a value of 0 for a while the highest possible respiratory rate (or respiratory volume, temperature, etc.) may be correlated to a value of 1 for a. For example, a value of 1 for a may correspond to a respiratory rate of 1 breath per second or to a respiratory volume of 4 liters/second.

Referring again to FIG. 1, as represented by block 114 a cardiac output calculator 222 provides an indication of cardiac output based on some or all of the information described above. For example, the cardiac output calculator 222 may utilize the Fick equation to generate an estimate of cardiac output based on sensed or defined $SvO_2$, $SaO_2$, and hemoglobin parameters, and the activity-adapted BMR information.

As will be discussed in conjunction with FIGS. 3-6 below, the derived cardiac output information may be used to identify or track the condition of a patient and to determine appropriate therapy to be prescribed for the patient. Here, the cardiac output information may be used directly or may be used to obtain other information. For example, in some embodiments cardiac output may be used to estimate stroke volume. Here, the stroke volume may be calculated by dividing the cardiac output by the heart rate.

Figure 3:
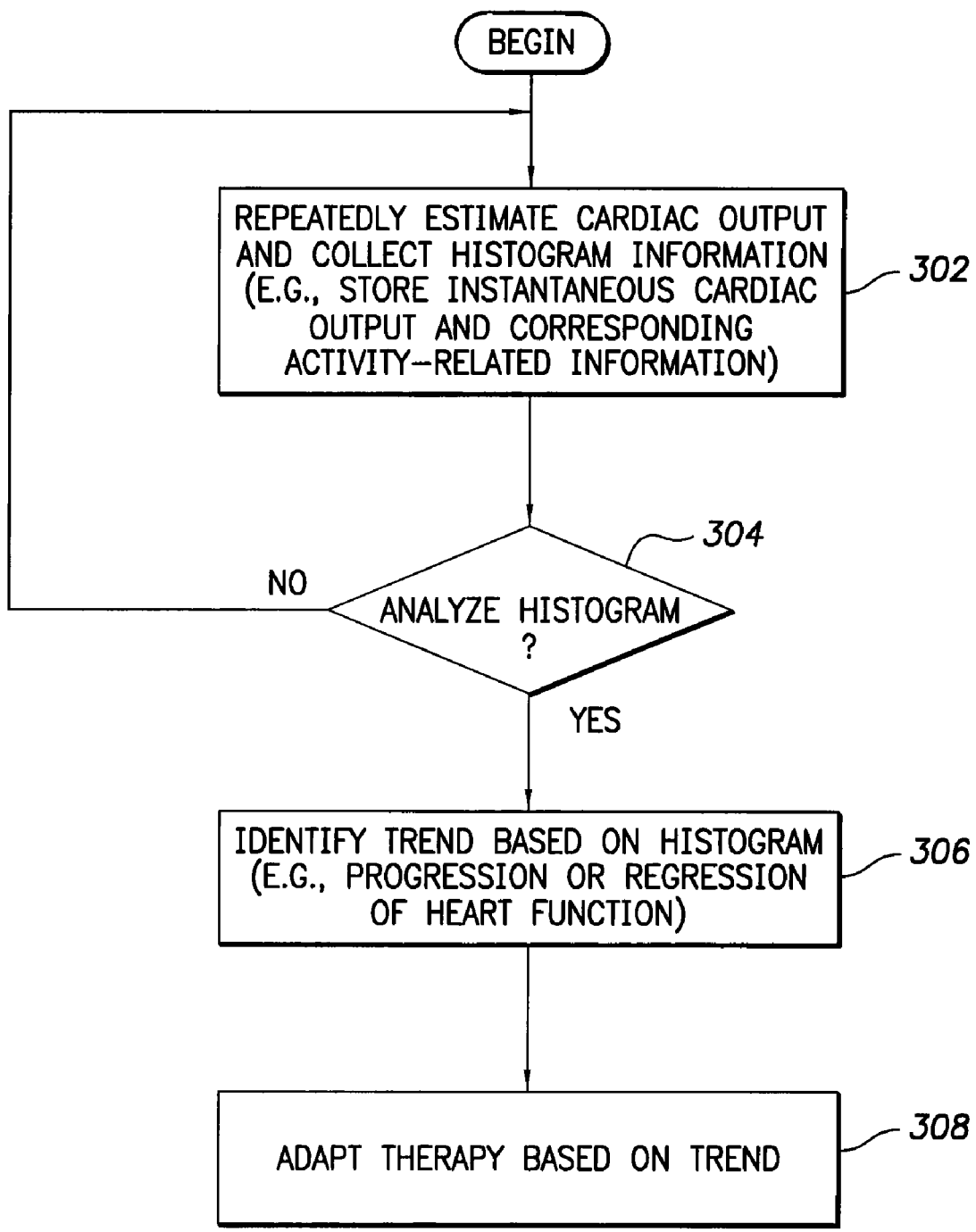
FIG. 3 is a simplified flowchart of an embodiment of operations that may be performed to adapt therapy based on cardiac output information.

Referring now to FIGS. 2 and 3, in some embodiments the system 200 may include a histogram generator 224 that generates a histogram 226 of the instantaneous cardiac output information derived by the cardiac output calculator 222. For example, as represented by block 302 the system 200 may be configured to assess metabolic rate over a period of time (e.g., throughout the day). In addition, each of these assessments may be associated with a corresponding level of patient activity as mentioned above. For example, the cardiac output estimates may be made during rest and during various levels of exercise (e.g. including maximum exercise). A histogram generator 224 may therefore store histogram information 226 based on these estimates, whereby the information 226 may provide medical personnel with an understanding of the range of the patient's cardiac performance and/or the capability of the patient's cardiac performance.

As represented by block 304, the histogram information may be analyzed on a repeated basis. For example, histogram information may be collected for a given period of time (e.g., daily, biweekly, weekly, monthly, or some other time period), after which the system 200 may analyze the collected histogram information.

Accordingly, as represented by block 306, a trend analyzer 228 (FIG. 2) may process the histogram information 226 on a repeated basis (e.g., daily, biweekly, weekly, monthly) to identify any trends that may be indicated by the histogram information 226. Such a trend may indicate progression of a patient's heart function (e.g., progression of heart failure) or may indicate regression of the patient's heart function (e.g., regression of heart failure). As an example, the histogram information 226 may indicate whether there is an increase or decrease over time in the amount of time per day that the patient is able to achieve a maximal level of activity (e.g., the highest 1% activity level). Similarly, the histogram information 226 may indicate whether there is an increase or decrease over time in the level of activity that the patient is able to achieve. Also, the histogram information 226 may relate to the mean activity-level of the patient over time. In general, an increase in parameters such as these may thereby indicate that the patient's health is improving. Conversely, a decrease in such parameters may indicate that the patient's health is getting worse. It should be appreciated that a trend may be based on various types of histogram information. For example, in some implementations trends may be identified based on minimum histogram values.

As represented by block 308 of FIG. 3, a therapy module 230 (FIG. 2) may define (e.g., adapt) therapy for the patient based on the histogram information 226 (e.g., based on any trends identified by the trend analyzer 228). For example, in the event the current therapy prescribed for the patient does not result in an improvement in the patient's condition, the therapy module 230 may alter the prescribed therapy. Adaptation of therapy may include, in some implementations, modifying cardiac resynchronization therapy, adjusting pacing parameters, prescribing a drug, changing currently prescribed drug therapy, or providing some other suitable change in treatment.

In some implementations the information described herein may be provided to an external device (e.g., a device located external to a patient). In this way, the external device may analyze the data and/or alert medical personnel as to the results of the cardiac output-related operations. For example, information and/or warning signals may be transmitted to a bedside monitor that generates audible or visual warnings. The bedside monitor may be networked with other external systems so as to automatically forward the information and/or warnings to a physician or other medical professional. An example of a system incorporating bedside monitoring units connected to a centralized external programmer system is described in U.S. Pat. No. 6,622,045, the disclosure of which is hereby incorporated by reference herein.

Figure 4:
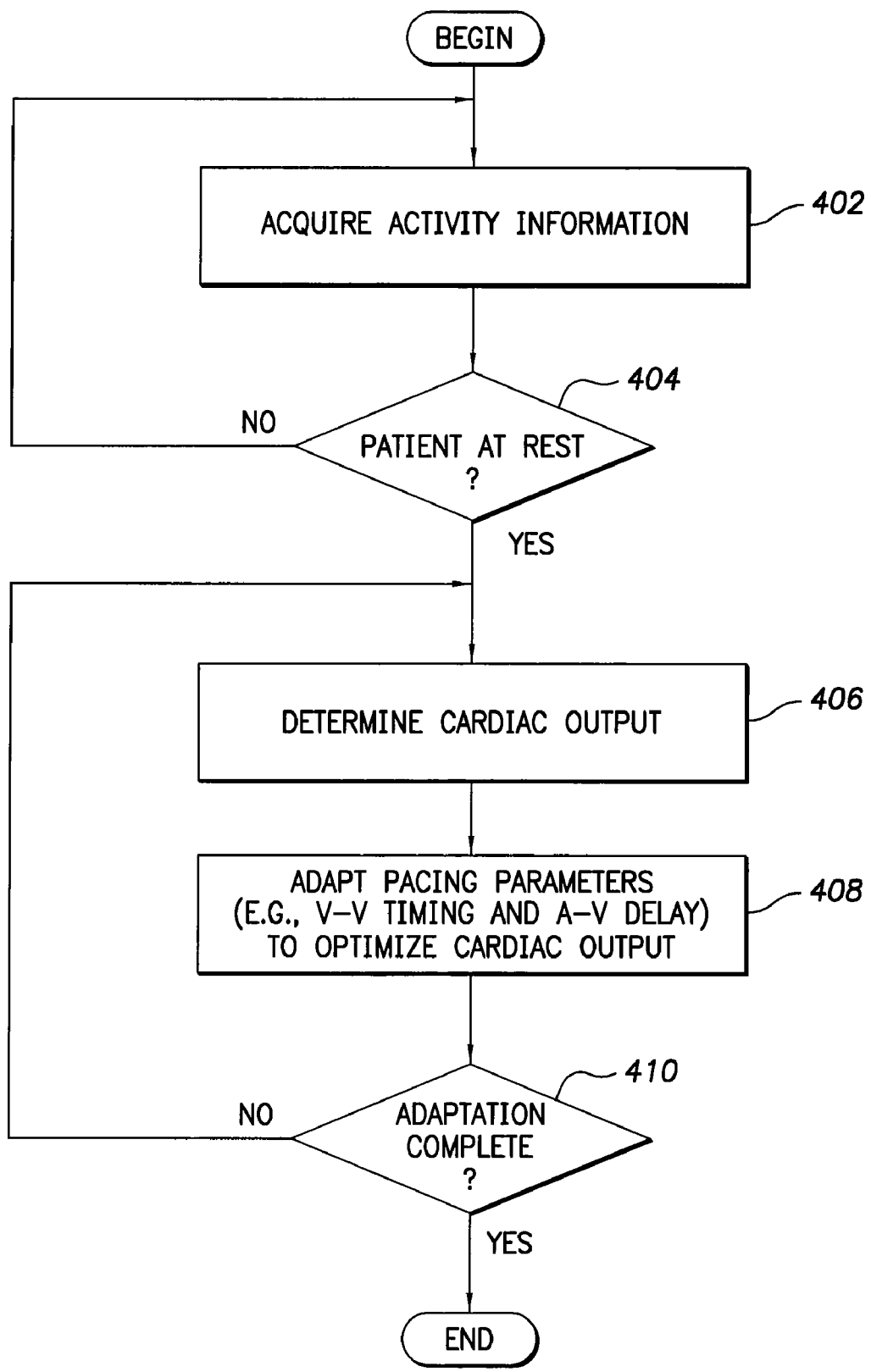
FIG. 4 is a simplified flowchart of an embodiment of operations that may be performed to adapt pacing parameters based on cardiac output information.
Figure 5:
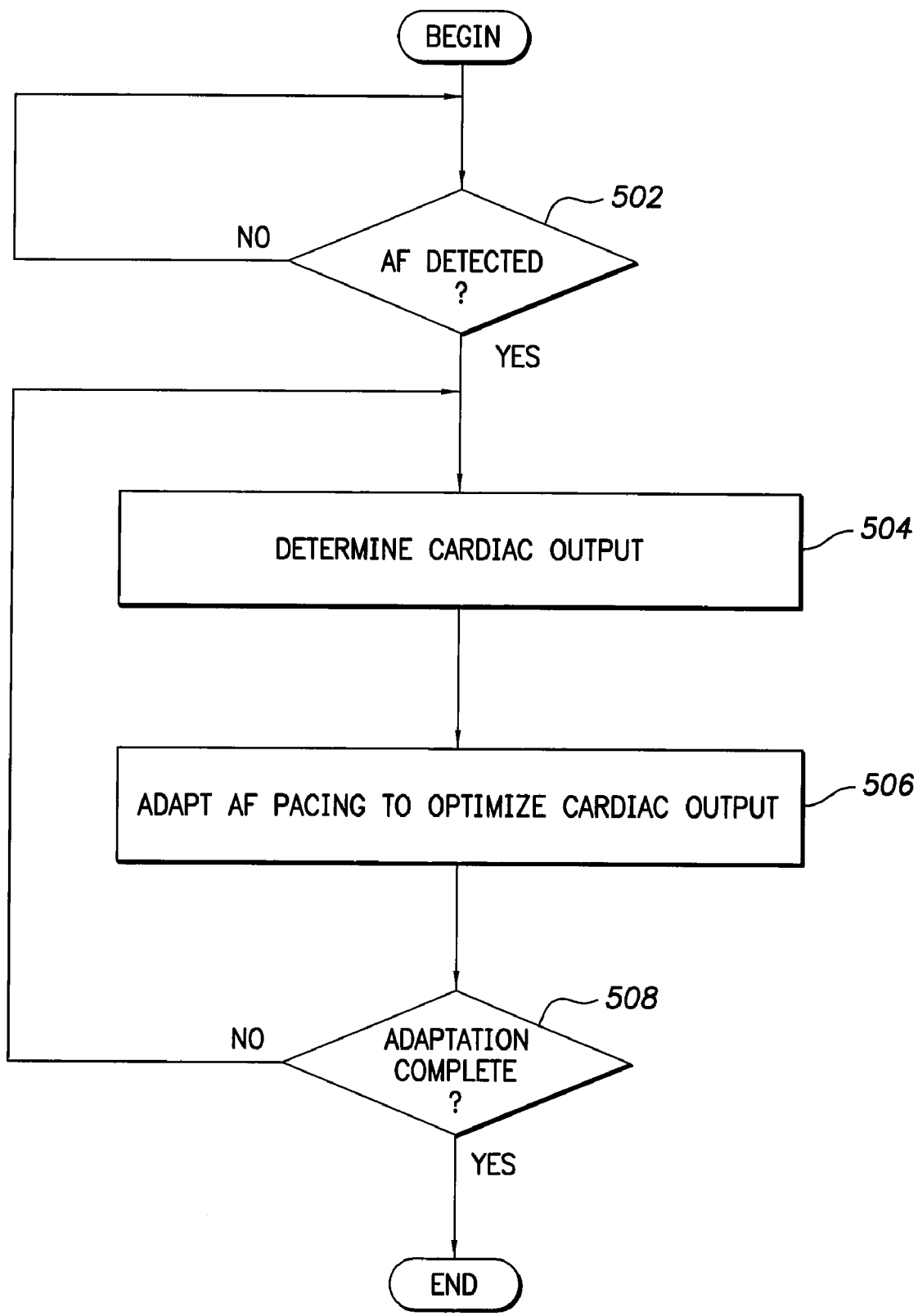
FIG. 5 is a simplified flowchart of an embodiment of operations that may be performed to adapt atrial fibrillation pacing based on cardiac output information.

Referring now to FIG. 4, in some embodiments cardiac pacing parameters may be adapted based on indications of cardiac output generated, for example, in the manner above described in conjunction with FIG. 1. As represented by blocks 402 and 404, in some embodiments pacing parameters for a patient may be adapted when the patient is at rest. Accordingly, at block 402 a component of a monitoring system (e.g., the system 200) may acquire activity-related information (e.g., as taught herein) to determine whether the patient is at rest.

As represented by block 406, when the patient is at rest, the monitoring system (e.g., comprising the cardiac output calculator 222) may determine (e.g., estimate) the current cardiac output of the patient. This may be accomplished, for example, using the Fick equation as taught herein or in some other manner.

As represented by block 408 the system 200 (e.g., the therapy module 230) may adapt the cardiac pacing parameters based on a current cardiac output estimate provided by, for example, the cardiac output calculator 222. Such pacing parameters may include, for example, ventricle-to-ventricle ("V-V") timing, atrio-ventricular ("A-V") delay, or some other suitable pacing parameter.

As represented by block 410, the operations of blocks 406 and 408 may be repeated as necessary to identify a set of pacing parameters that result in optimal cardiac output or that achieve some other cardiac output-based target. The adaptation of pacing parameters may be performed, for example, in a similar manner as described in U.S. Pat. No. 5,891,176 that describes techniques for optimizing various pacing parameters, the disclosure of which is hereby incorporated by reference herein. In some implementations different parameters may be defined for different levels of patient activity.

In some embodiments cardiac pacing to be employed during atrial fibrillation ("AF") may be adapted based on indications of cardiac output generated, for example, in the manner described above in conjunction with FIG. 1. In some scenarios, adaptation of cardiac pacing in this way may provide a more effective method of treating atrial fibrillation. Accordingly, as represented by block 502 in FIG. 5, a component of a monitoring system (e.g., as described below in conjunction with FIG. 8) may monitor cardiac signals (e.g., IEGM data) to determine whether the patient is experiencing an episode of atrial fibrillation.

As represented by block 504, in the event atrial fibrillation is detected, the monitoring system (e.g., comprising the cardiac output calculator 222) may monitor the current cardiac output of the patient. Again, this may be accomplished using the Fick equation as taught herein or in some other manner.

As represented by block 506 the monitoring system (e.g., the therapy module 230) may adapt cardiac pacing based on the current cardiac output estimate provided by, for example, the cardiac output calculator 222. For example, the therapy module 230 may adjust the rate at which the ventricle is being paced during atrial fibrillation, and the V-V timing, if the system is a biventricular pacing system.

As represented by block 508, the operations of blocks 504 and 506 may be repeated as necessary (e.g., over a defined period of time such as one minute) to identify one or more pacing parameters that result in optimal cardiac output or that achieve some other cardiac output-based target. The optimization of such a parameter may, in turn, result in a more effective treatment of atrial fibrillation. Again, in some implementations different pacing parameters may be defined for different levels of patient activity.

Figure 6:
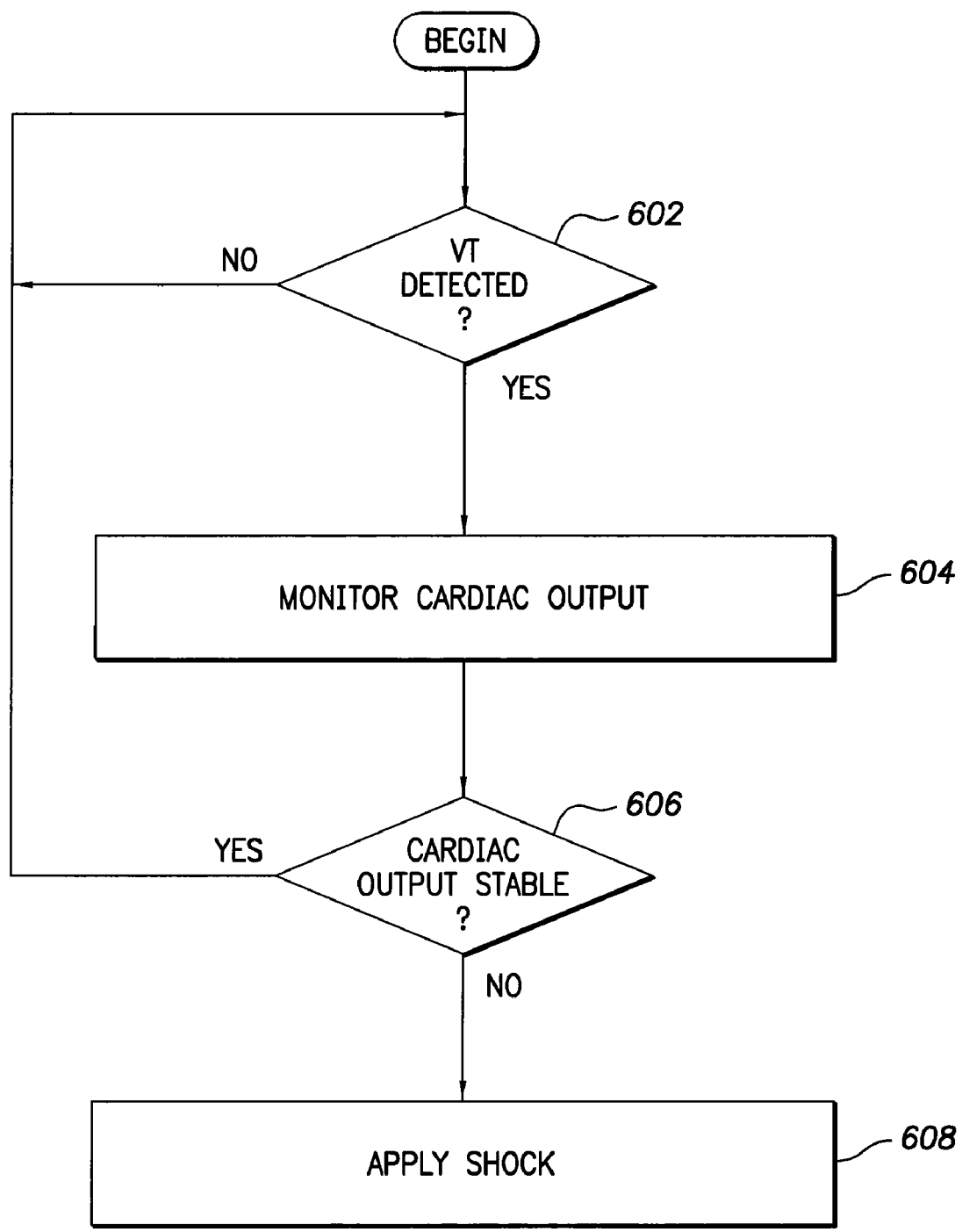
FIG. 6 is a simplified flowchart of an embodiment of operations that may be performed to adapt ventricular tachyarrhythmia therapy based on cardiac output information.

Referring now to FIG. 6, in some embodiments cardiac output may be monitored to determine whether to apply a shock to treat an arrhythmia such as ventricular tachycardia ("VT"). As represented by block 602, a component of a monitoring system (e.g., as described below in conjunction with FIG. 8) may monitor cardiac signals (e.g., IEGM data) to determine whether the patient is experiencing an episode of ventricular tachycardia.

As represented by block 604, in the event ventricular tachycardia is detected, the monitoring system (e.g., comprising the cardiac output calculator 222) may monitor the current cardiac output of the patient using the Fick equation as taught herein or in some other manner. As represented by block 606, the monitoring system (e.g., the trend analyzer 228) may determine whether the cardiac output is relatively (e.g., substantially) stable over a given period of time. If the cardiac output is relatively stable (e.g., the patient is experiencing a hemodynamically stable arrhythmia), a determination may be made (e.g., by the therapy module 230) that the current episode of ventricular tachyarrhythmia is not to be treated with a shock but may instead be treated, for example, using anti-tachycardia pacing ("ATP"). Accordingly, the operational flow may proceed back to blocks 602 and 604 to continue monitoring for ventricular tachycardia and cardiac output during such episodes.

In some implementations, similar operations may be employed in conjunction with detection of atrial fibrillation as described above in conjunction with FIG. 5. For example, if cardiac output is relatively stable during atrial fibrillation a decision may be made to not apply a shock and to instead continue anti-tachycardia pacing ("ATP").

As represented by block 608, in the event cardiac output is not stable during ventricular tachycardia (e.g., for a given period of time), the therapy module 230 may cause a shock to be delivered to the heart of the patient. This may be accomplished, for example, in the manner described below in conjunction with FIGS. 7 and 8.

Exemplary Cardiac Device

As mentioned above, in some embodiments one or more of the components taught herein may be implemented in an implantable medical device. The following description sets forth an exemplary implantable cardiac device (e.g., a stimulation device such as an implantable cardioverter defibrillator, a pacemaker, etc.) that is capable of being used in connection with the various embodiments that are described herein. It is to be appreciated and understood that other medical devices, including those that are not necessarily implantable, can be used and that the description below is given, in its specific context, to assist the reader in understanding, with more clarity, the embodiments described herein.

Figure 7:
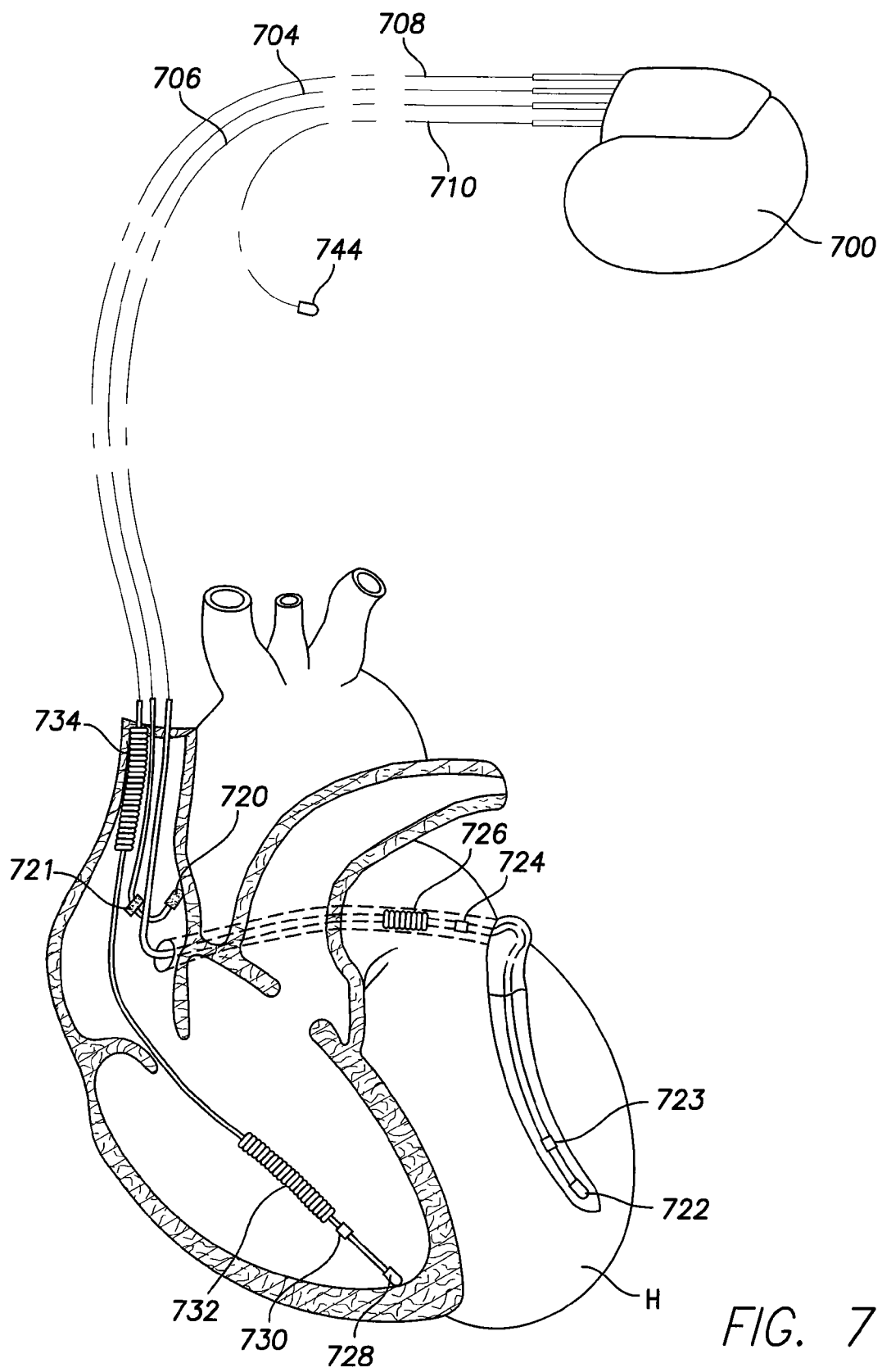
FIG. 7 is a simplified diagram of an embodiment of an implantable stimulation device in electrical communication with one or more leads implanted in a patient's heart for sensing conditions in the patient, delivering therapy to the patient, or providing some combination thereof.

FIG. 7 shows an exemplary implantable cardiac device 700 in electrical communication with a patient's heart H by way of three leads 704, 706, and 708, suitable for delivering multichamber stimulation and shock therapy. To sense atrial cardiac signals and to provide right atrial chamber stimulation therapy, the device 700 is coupled to an implantable right atrial lead 704 having, for example, an atrial tip electrode 720, which typically is implanted in the patient's right atrial appendage or septum. FIG. 7 also shows the right atrial lead 704 as having an optional atrial ring electrode 721.

To sense left atrial and ventricular cardiac signals and to provide left chamber pacing therapy, the device 700 is coupled to a coronary sinus lead 706 designed for placement in the coronary sinus region via the coronary sinus for positioning one or more electrodes adjacent to the left ventricle, one or more electrodes adjacent to the left atrium, or both. As used herein, the phrase "coronary sinus region" refers to the vasculature of the left ventricle, including any portion of the coronary sinus, the great cardiac vein, the left marginal vein, the left posterior ventricular vein, the middle cardiac vein, the small cardiac vein or any other cardiac vein accessible by the coronary sinus.

Accordingly, an exemplary coronary sinus lead 706 is designed to receive atrial and ventricular cardiac signals and to deliver left ventricular pacing therapy using, for example, a left ventricular tip electrode 722 and, optionally, a left ventricular ring electrode 723; provide left atrial pacing therapy using, for example, a left atrial ring electrode 724; and provide shocking therapy using, for example, a left atrial coil electrode 726 (or other electrode capable of delivering a shock). For a more detailed description of a coronary sinus lead, the reader is directed to U.S. Pat. No. 5,466,254, "Coronary Sinus Lead with Atrial Sensing Capability" (Helland), which is incorporated herein by reference.

The device 700 is also shown in electrical communication with the patient's heart H by way of an implantable right ventricular lead 708 having, in this implementation, a right ventricular tip electrode 728, a right ventricular ring electrode 730, a right ventricular (RV) coil electrode 732 (or other electrode capable of delivering a shock), and a superior vena cava (SVC) coil electrode 734 (or other electrode capable of delivering a shock). Typically, the right ventricular lead 708 is transvenously inserted into the heart H to place the right ventricular tip electrode 728 in the right ventricular apex so that the RV coil electrode 732 will be positioned in the right ventricle and the SVC coil electrode 734 will be positioned in the superior vena cava. Accordingly, the right ventricular lead 708 is capable of sensing or receiving cardiac signals, and delivering stimulation in the form of pacing and shock therapy to the right ventricle.

The device 700 is also shown in electrical communication with a lead 710 including one or more components 744 such as a physiologic sensor (e.g., one or more activity-related acquisition components as described herein). The component(s) 744 may be positioned in, near or remote from the heart.

It should be appreciated that the device 700 may connect to leads other than those specifically shown. In addition, the leads connected to the device 700 may include components other than those specifically shown. For example, a lead may include other types of electrodes, sensors or devices that serve to otherwise interact with a patient or the surroundings.

Figure 8:
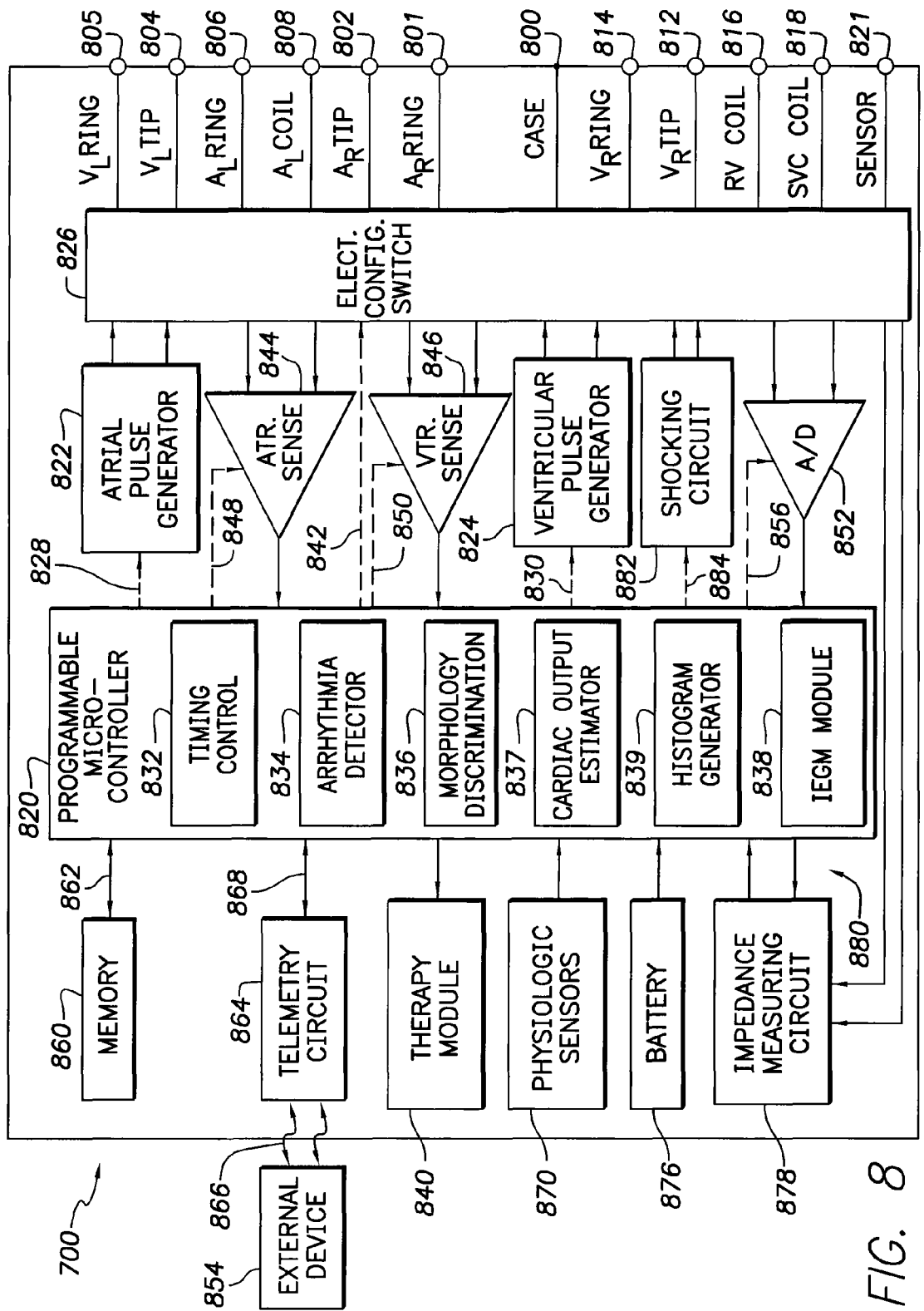
FIG. 8 is a simplified functional block diagram of an embodiment of an implantable cardiac device, illustrating basic elements that may be configured to sense conditions in the patient, deliver therapy to the patient, or provide some combination thereof.

FIG. 8 depicts an exemplary, simplified block diagram illustrating sample components of the device 700. The device 700 may be adapted to treat both fast and slow arrhythmias with stimulation therapy, including cardioversion, defibrillation, and pacing stimulation. While a particular multi-chamber device is shown, it is to be appreciated and understood that this is done for illustration purposes. Thus, the techniques and methods described below can be implemented in connection with any suitably configured or configurable device. Accordingly, one of skill in the art could readily duplicate, eliminate, or disable the appropriate circuitry in any desired combination to provide a device capable of treating the appropriate chamber(s) with, for example, cardioversion, defibrillation, and pacing stimulation.

Housing 800 for the device 700 is often referred to as the "can", "case" or "case electrode", and may be programmably selected to act as the return electrode for all "unipolar" modes. The housing 800 may further be used as a return electrode alone or in combination with one or more of the coil electrodes 726, 732 and 734 for shocking purposes. Housing 800 further includes a connector (not shown) having a plurality of terminals 801, 802, 804, 805, 806, 808, 812, 814, 816 and 818 (shown schematically and, for convenience, the names of the electrodes to which they are connected are shown next to the terminals). The connector may be configured to include various other terminals depending on the requirements of a given application. For example, one or more terminals 821 may each be coupled to a sensor (e.g., component 744) or some other component.

To achieve right atrial sensing and pacing, the connector includes, for example, a right atrial tip terminal (AR TIP) 802 adapted for connection to the right atrial tip electrode 720. A right atrial ring terminal (AR RING) 801 may also be included and adapted for connection to the right atrial ring electrode 721. To achieve left chamber sensing, pacing, and shocking, the connector includes, for example, a left ventricular tip terminal (VL TIP) 804, a left ventricular ring terminal (VL RING) 805, a left atrial ring terminal (AL RING) 806, and a left atrial shocking terminal (AL COIL) 808, which are adapted for connection to the left ventricular tip electrode 722, the left ventricular ring electrode 723, the left atrial ring electrode 724, and the left atrial coil electrode 726, respectively.

To support right chamber sensing, pacing, and shocking, the connector further includes a right ventricular tip terminal (VR TIP) 812, a right ventricular ring terminal (VR RING) 814, a right ventricular shocking terminal (RV COIL) 816, and a superior vena cava shocking terminal (SVC COIL) 818, which are adapted for connection to the right ventricular tip electrode 728, the right ventricular ring electrode 730, the RV coil electrode 732, and the SVC coil electrode 734, respectively.

At the core of the device 700 is a programmable microcontroller 820 that controls the various modes of stimulation therapy. As is well known in the art, microcontroller 820 typically includes a microprocessor, or equivalent control circuitry, designed specifically for controlling the delivery of stimulation therapy, and may further include memory such as RAM, ROM and flash memory, logic and timing circuitry, state machine circuitry, and I/O circuitry. Typically, microcontroller 820 includes the ability to process or monitor input signals (data or information) as controlled by a program code stored in a designated block of memory. The type of microcontroller is not critical to the described implementations. Rather, any suitable microcontroller 820 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals that may be used within the device and their inter-relationship, see U.S. Pat. No. 4,788,980 (Mann et al.), also incorporated herein by reference.

FIG. 8 also shows an atrial pulse generator 822 and a ventricular pulse generator 824 that generate pacing stimulation pulses for delivery by the right atrial lead 704, the coronary sinus lead 706, the right ventricular lead 708, or some combination of these leads via an electrode configuration switch 826. It is understood that in order to provide stimulation therapy in each of the four chambers of the heart, the atrial and ventricular pulse generators 822 and 824 may include dedicated, independent pulse generators, multiplexed pulse generators, or shared pulse generators. The pulse generators 822 and 824 are controlled by the microcontroller 820 via appropriate control signals 828 and 830, respectively, to trigger or inhibit the stimulation pulses.

Microcontroller 820 further includes timing control circuitry 832 to control the timing of the stimulation pulses (e.g., pacing rate, atrio-ventricular (A-V) delay, atrial interconduction (A-A) delay, or ventricular interconduction (V-V) delay, etc.) or other operations, as well as to keep track of the timing of refractory periods, blanking intervals, noise detection windows, evoked response windows, alert intervals, marker channel timing, etc., as known in the art.

Microcontroller 820 further includes an arrhythmia detector 834. The arrhythmia detector 834 may be utilized by the device 700 for determining desirable times to administer various therapies. The arrhythmia detector 834 may be implemented, for example, in hardware as part of the microcontroller 820, or as software/firmware instructions programmed into the device 700 and executed on the microcontroller 820 during certain modes of operation.

Microcontroller 820 may include a morphology discrimination module 836, a capture detection module 837 and an auto sensing module 838. These modules are optionally used to implement various exemplary recognition algorithms or methods. The aforementioned components may be implemented, for example, in hardware as part of the microcontroller 820, or as software/firmware instructions programmed into the device 700 and executed on the microcontroller 820 during certain modes of operation.

The electrode configuration switch 826 includes a plurality of switches for connecting the desired terminals (e.g., that are connected to electrodes, coils, sensors, etc.) to the appropriate I/O circuits, thereby providing complete terminal and, hence, electrode programmability. Accordingly, switch 826, in response to a control signal 842 from the microcontroller 820, may be used to determine the polarity of the stimulation pulses (e.g., unipolar, bipolar, combipolar, etc.) by selectively closing the appropriate combination of switches (not shown) as is known in the art.

Atrial sensing circuits (ATR. SENSE) 844 and ventricular sensing circuits (VTR. SENSE) 846 may also be selectively coupled to the right atrial lead 704, coronary sinus lead 706, and the right ventricular lead 708, through the switch 826 for detecting the presence of cardiac activity in each of the four chambers of the heart. Accordingly, the atrial and ventricular sensing circuits 844 and 846 may include dedicated sense amplifiers, multiplexed amplifiers, or shared amplifiers. Switch 826 determines the "sensing polarity" of the cardiac signal by selectively closing the appropriate switches, as is also known in the art. In this way, the clinician may program the sensing polarity independent of the stimulation polarity. The sensing circuits (e.g., circuits 844 and 846) are optionally capable of obtaining information indicative of tissue capture.

Each sensing circuit 844 and 846 preferably employs one or more low power, precision amplifiers with programmable gain, automatic gain control, bandpass filtering, a threshold detection circuit, or some combination of these components, to selectively sense the cardiac signal of interest. The automatic gain control enables the device 700 to deal effectively with the difficult problem of sensing the low amplitude signal characteristics of atrial or ventricular fibrillation.

The outputs of the atrial and ventricular sensing circuits 844 and 846 are connected to the microcontroller 820, which, in turn, is able to trigger or inhibit the atrial and ventricular pulse generators 822 and 824, respectively, in a demand fashion in response to the absence or presence of cardiac activity in the appropriate chambers of the heart. Furthermore, as described herein, the microcontroller 820 is also capable of analyzing information output from the sensing circuits 844 and 846, a data acquisition system 852, or both. This information may be used to determine or detect whether and to what degree tissue capture has occurred and to program a pulse, or pulses, in response to such determinations. The sensing circuits 844 and 846, in turn, receive control signals over signal lines 848 and 850, respectively, from the microcontroller 820 for purposes of controlling the gain, threshold, polarization charge removal circuitry (not shown), and the timing of any blocking circuitry (not shown) coupled to the inputs of the sensing circuits 844 and 846 as is known in the art.

For arrhythmia detection, the device 700 utilizes the atrial and ventricular sensing circuits 844 and 846 to sense cardiac signals to determine whether a rhythm is physiologic or pathologic. It should be appreciated that other components may be used to detect arrhythmia depending on the system objectives. In reference to arrhythmias, as used herein, "sensing" is reserved for the noting of an electrical signal or obtaining data (information), and "detection" is the processing (analysis) of these sensed signals and noting the presence of an arrhythmia.

Timing intervals between sensed events (e.g., P-waves, R-waves, and depolarization signals associated with fibrillation) may be classified by the arrhythmia detector 834 of the microcontroller 820 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules may be applied to the atrial channel to determine if there is an atrial tachyarrhythmia or atrial fibrillation with appropriate classification and intervention.

Cardiac signals or other signals may be applied to inputs of an analog-to-digital (A/D) data acquisition system 852. The data acquisition system 852 is configured (e.g., via signal line 856) to acquire intracardiac electrogram ("IEGM") signals or other signals, convert the raw analog data into a digital signal, and store the digital signals for later processing, for telemetric transmission to an external device 854, or both. For example, the data acquisition system 852 may be coupled to the right atrial lead 704, the coronary sinus lead 706, the right ventricular lead 708 and other leads through the switch 826 to sample cardiac signals across any pair of desired electrodes.

The data acquisition system 852 also may be coupled to receive signals from other input devices. For example, the data acquisition system 852 may sample signals from a physiologic sensor 870 or other components shown in FIG. 8 (connections not shown).

The microcontroller 820 is further coupled to a memory 860 by a suitable data/address bus 862, wherein the programmable operating parameters used by the microcontroller 820 are stored and modified, as required, in order to customize the operation of the device 700 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart H within each respective tier of therapy. One feature of the described embodiments is the ability to sense and store a relatively large amount of data (e.g., from the data acquisition system 852), which data may then be used for subsequent analysis to guide the programming of the device 700.

Advantageously, the operating parameters of the implantable device 700 may be non-invasively programmed into the memory 860 through a telemetry circuit 864 in telemetric communication via communication link 866 with the external device 854, such as a programmer, transtelephonic transceiver, a diagnostic system analyzer or some other device. The microcontroller 820 activates the telemetry circuit 864 with a control signal (e.g., via bus 868). The telemetry circuit 864 advantageously allows intracardiac electrograms and status information relating to the operation of the device 700 (as contained in the microcontroller 820 or memory 860) to be sent to the external device 854 through an established communication link 866.

The device 700 can further include one or more physiologic sensors 870. In some embodiments the device 700 may include a "rate-responsive" sensor that may provide, for example, information to aid in adjustment of pacing stimulation rate according to the exercise state of the patient. One or more physiologic sensors 870 (e.g., a pressure sensor) may further be used to detect changes in cardiac output, changes in the physiological condition of the heart, or diurnal changes in activity (e.g., detecting sleep and wake states). Accordingly, the microcontroller 820 responds by adjusting the various pacing parameters (such as rate, A-V Delay, V-V Delay, etc.) at which the atrial and ventricular pulse generators 822 and 824 generate stimulation pulses.

While shown as being included within the device 700, it is to be understood that a physiologic sensor 870 may also be external to the device 700, yet still be implanted within or carried by the patient. Examples of physiologic sensors that may be implemented in conjunction with the device 700 include sensors that sense respiratory rate (e.g., respiration rate), pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

The one or more physiologic sensors 870 may optionally include one or more of components to help detect movement (via, e.g., a position sensor or an accelerometer) and minute ventilation (via an MV sensor) in the patient. Signals generated by the position sensor and MV sensor may be passed to the microcontroller 820 for analysis in determining whether to adjust the pacing rate, etc. The microcontroller 820 may thus monitor the signals for indications of the patient's position and activity status, such as whether the patient is climbing up stairs or descending down stairs or whether the patient is sitting up after lying down.

The device 700 additionally includes a battery 876 that provides operating power to all of the circuits shown in FIG. 8. For a device 700 which employs shocking therapy, the battery 876 is capable of operating at low current drains (e.g., preferably less than 10 µA) for long periods of time, and is capable of providing high-current pulses (for capacitor charging) when the patient requires a shock pulse (e.g., preferably, in excess of 2 A, at voltages above 200 V, for periods of 10 seconds or more). The battery 876 also desirably has a predictable discharge characteristic so that elective replacement time can be detected. Accordingly, the device 700 preferably employs lithium or other suitable battery technology.

The device 700 can further include magnet detection circuitry (not shown), coupled to the microcontroller 820, to detect when a magnet is placed over the device 700. A magnet may be used by a clinician to perform various test functions of the device 700 and to signal the microcontroller 820 that the external device 854 is in place to receive data from or transmit data to the microcontroller 820 through the telemetry circuit 864.

The device 700 further includes an impedance measuring circuit 878 that is enabled by the microcontroller 820 via a control signal 880. The known uses for an impedance measuring circuit 878 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device 700 has been implanted; measuring stroke volume; and detecting the opening of heart valves, etc. The impedance measuring circuit 878 is advantageously coupled to the switch 826 so that any desired electrode may be used.

In the case where the device 700 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 820 further controls a shocking circuit 882 by way of a control signal 884. The shocking circuit 882 generates shocking pulses of low (e.g., up to 0.5 J), moderate (e.g., 0.5 J to 10 J), or high energy (e.g., 11 J to 40 J), as controlled by the microcontroller 820. Such shocking pulses are applied to the patient's heart H through, for example, two shocking electrodes and as shown in this embodiment, selected from the left atrial coil electrode 726, the RV coil electrode 732 and the SVC coil electrode 734. As noted above, the housing 800 may act as an active electrode in combination with the RV coil electrode 732, as part of a split electrical vector using the SVC coil electrode 734 or the left atrial coil electrode 726 (i.e., using the RV electrode as a common electrode), or in some other arrangement.

Cardioversion level shocks are generally considered to be of low to moderate energy level (so as to minimize pain felt by the patient), be synchronized with an R-wave, pertain to the treatment of tachycardia, or some combination of the above. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 820 is capable of controlling the synchronous or asynchronous delivery of the shocking pulses.

As mentioned above, a device such as the device 700 may include several components that provide functionality as taught herein. For example, one or more of the switch 826, the sense circuits 844 and 846, the impedance measuring circuit 878, the physiologic sensors 870, and the data acquisition system 852 may acquire signals (e.g., activity-related signals) that are used in the operations discussed above. The data described above may be stored in the data memory 860. In addition, a therapy module 840 may be configured to analyze cardiac output information and to adapt or otherwise facilitate the administration of therapy for a patient (e.g., control pacing).

The microcontroller 820 (e.g., a processor providing signal processing functionality) also may implement or support at least a portion of the functionality discussed herein. For example, an IEGM module 838 may generate IEGM data that is processed to identify respiration-related information, heart rate information, and arrhythmia (e.g., atrial fibrillation or ventricular tachycardia) information. A histogram generator 839 may generate histogram information. A cardiac output estimator 837 may provide functionality of one or more the components of FIG. 2 (e.g., components 218-222). A telemetry circuit 864 may provide functionality for programming various parameters as discussed herein into the device 700. An arrhythmia detector 834 may detect arrhythmia (e.g., atrial fibrillation or ventricular tachycardia) as discussed herein.

It should be appreciated that the disclosed embodiments may be modified in various ways based on the teachings herein. For example, the structure and functionality taught herein may be incorporated into types of devices other than the specific types of devices described above. In addition, various techniques may be used to obtain various types of activity-related information, and various techniques may be employed to generate oxygen consumption-related information and cardiac output-related information. Furthermore, various operations may be performed based on the derived cardiac output information.

It should be appreciated from the above that the various structures and functions described herein may be incorporated into a variety of apparatuses (e.g., a stimulation device, a lead, a monitoring device, etc.) and implemented in a variety of ways. Different embodiments of such an apparatus may include a variety of hardware and software processing components. In some embodiments, hardware components such as processors, controllers, state machines, logic, or some combination of these components, may be used to implement the described components or circuits.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

Moreover, some of the operations described herein may be performed by a device that is located externally with respect to the body of the patient. For example, an implanted device may send raw data or processed data to an external device that then performs the necessary processing.

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

The signals discussed herein may take various forms. For example, in some embodiments a signal may comprise electrical signals transmitted over a wire, light pulses transmitted through an optical medium such as an optical fiber or air, or RF waves transmitted through a medium such as air, and so on. In addition, a plurality of signals may be collectively referred to as a signal herein. The signals discussed above also may take the form of data. For example, in some embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

Also, it should be understood that any reference to elements herein using a designation such as "first," "second," and so forth does not generally limit the quantity or order of those elements. Rather, these designations may be used herein as a convenient method of distinguishing between two or more different elements or instances of an element. Thus, a reference to first and second elements does not mean that only two elements may be employed there or that the first element must precede the second element in some manner. Also, unless stated otherwise a set of elements may comprise one or more elements.

While certain embodiments have been described above in detail and shown in the accompanying drawings, it is to be understood that such embodiments are merely illustrative of and not restrictive of the teachings herein. In particular, it should be recognized that the teachings herein apply to a wide variety of apparatuses and methods. It will thus be recognized that various modifications may be made to the illustrated embodiments or other embodiments, without departing from the broad inventive scope thereof. In view of the above it will be understood that the teachings herein are intended to cover any changes, adaptations or modifications which are within the scope of the disclosure as defined by any claims associated herewith.

What is claimed is:

1. A method of identifying a heart function trend, said method comprising:
   acquiring venous oxygen saturation information via an implantable sensor;
   acquiring arterial oxygen saturation information;
   calculating estimates of oxygen consumption by multiplying a basic metabolic rate (BMR) by an activity based parameter;
   deriving a series of cardiac output measurements based on the venous oxygen saturation information, the estimates of oxygen consumption, and the arterial oxygen saturation information; and
   generating a histogram of cardiac output measurements as a function of activity level.

2. The method of claim 1, wherein the activity based parameter comprises an acceleration-based factor.

3. The method of claim 1, wherein the activity based parameter comprises a respiratory-based factor.

4. The method of claim 3 wherein the respiratory-based factor comprises one of respiratory rate, respiratory volume and minute ventilation.

5. The method of claim 1, further comprising identifying a trend in cardiac output as a function of activity level; and adapting cardiac therapy based on the identified trend.

6. The method of claim 1, further comprising acquiring hemoglobin-related information via a third implantable sensor, wherein the derivation of cardiac output measurements is further based on the hemoglobin-related information.

7. A method of deriving an indication of cardiac output by an implantable medical device, said method comprising:
   acquiring venous oxygen saturation information via a first implantable sensor;
   acquiring hemoglobin-related information via a second implantable sensor;
   calculating estimates of oxygen consumption by multiplying a basic metabolic rate (BMR) by an activity based parameter; and
   deriving cardiac output measurements based on the venous oxygen saturation information, the hemoglobin-related information, and the estimates of oxygen consumption.

8. The method of claim 7, wherein the second implantable sensor comprises an optical sensor.

9. The method of claim 7, wherein the second implantable sensor comprises an impedance sensor.

10. The method of claim 7, further comprising determining a pacing rate during atrial fibrillation based on the cardiac output measurements.

11. The method of claim 7, further comprising not administering a shock during ventricular tachyarrhythmia if the cardiac output measurements indicate that cardiac output is substantially stable.

12. The method of claim 7, further comprising:
    determining whether a patient is at rest; and
    adjusting at least one pacing parameter based on the cardiac output measurements to optimize cardiac output.

13. The method of claim 7, further comprising:
    generating a histogram of the cardiac output measurements as a function of the hemoglobin-related information;
    identifying a trend in the cardiac output measurements based on the histogram; and
    adapting treatment for a patient based on the identified trend.

14. An implantable medical device comprising:
    an implantable venous oxygen saturation sensor adapted to provide $S_V O2$ measurements;
    an implantable arterial oxygen saturation sensor adapted to provide $S_A O2$ measurements;
    an implantable hemoglobin sensor adapted to provide hemoglobin information;
    an oxygen consumption estimator adapted to calculate estimates of oxygen consumption by multiplying a basic metabolic rate (BMR) by an activity based parameter; and
    a cardiac output calculator adapted to derive an indication of cardiac output based on the $S_V O2$ measurements, the $S_A O2$ measurements, the hemoglobin information and the estimates of oxygen consumption.

* * * * *